(12) United States Patent
Sainani et al.

(10) Patent No.: US 8,889,898 B2
(45) Date of Patent: Nov. 18, 2014

(54) PROCESS FOR PREPARING DI-SUBSTITUTED SUCCINATES

(75) Inventors: Jaiprakash Brijlal Sainani, Baroda (IN); Mahesh Davadra, Vadodara (IN)

(73) Assignee: Saudi Basic Industries Corporation, Riyadh (SA)

(*) Notice: Subject to any disclaimer, the term of this patent is extended or adjusted under 35 U.S.C. 154(b) by 0 days.

(21) Appl. No.: 14/239,882

(22) PCT Filed: Aug. 23, 2012

(86) PCT No.: PCT/EP2012/003571
§ 371 (c)(1),
(2), (4) Date: Feb. 20, 2014

(87) PCT Pub. No.: WO2013/029767
PCT Pub. Date: Mar. 7, 2013

(65) Prior Publication Data
US 2014/0194647 A1   Jul. 10, 2014

(30) Foreign Application Priority Data
Aug. 29, 2011   (EP) .................................... 11007014

(51) Int. Cl.
| C07C 67/36 | (2006.01) |
| C07C 51/09 | (2006.01) |
| C07C 67/343 | (2006.01) |
| C07C 67/08 | (2006.01) |
| C08F 4/76 | (2006.01) |

(52) U.S. Cl.
CPC . C08F 4/76 (2013.01); C07C 51/09 (2013.01); C07C 67/343 (2013.01); C07C 67/08 (2013.01)
USPC .......................................... 560/204; 502/150

(58) Field of Classification Search
None
See application file for complete search history.

(56) References Cited

U.S. PATENT DOCUMENTS

| 4,579,836 A | 4/1986 | Azoumanidis et al. |
| 4,612,299 A | 9/1986 | Azroumanidis et al. |
| 5,567,665 A | 10/1996 | Wagner et al. |
| 6,268,306 B1 | 7/2001 | Zakharov et al. |
| 6,818,583 B1 * | 11/2004 | Morini et al. ................. 502/103 |
| 2003/0181743 A1 | 9/2003 | Morini et al. |

FOREIGN PATENT DOCUMENTS

| EP | 0653445 A1 | 5/1995 |
| EP | 1179529 A1 | 2/2002 |
| EP | 1336625 A1 | 8/2003 |
| EP | 0786466 A1 | 7/2014 |
| WO | 9635729 | 11/1996 |
| WO | 9845338 | 10/1998 |
| WO | 9845338 A1 | 10/1998 |
| WO | 0001736 | 1/2000 |

OTHER PUBLICATIONS

Armande, J. C. Lapierre, et al., "A simple approach to 12-azaprostaglandin congeners", Recueil, Journal of the Royal Netherlands Chemical Society, 99/3 (Mar. 1980) 87-91.

Inaba, Shin-ichi and Ojima, Iwao, "Novel and Convenient Route to Substituted Succinates. The Dimerization of Ketene Silyl Acetals Promoted by Titanium Tetrachloride", Tetrahedron Letters No. 23, pp. 2009-2012 (1977) Pergamon Press. Printed in Great Britain.

Kuo, Yu-Neng, et al., "The Reaction of Ester Enolates with Copper (II) Salts. A Synthesis of Substituted Succinate Esters", Journal of the American Chemical Society 93:18 1, 4605-4606 (Sep. 8, 1971).

Long, Nathan R. and Rathke, Michael W., "Isolation and Reactions of the Lithium Di-Enolate of Diethyl Succinate", Synthetic Communications, 11(9), 687-696 (1981).

Matsumura, Yoshihiro, et al., "Dependence of the Reactivities of Titanium Enolates on How They Are Generated: Diastereoselective Coupling of Phenylacetic Acid Esters Using Titanium Tetrachloride", J. Org. Chem. (1996) 61, 2809-2812.

Payot, P.H., "Die Alkylierung von Formylbernsteinsaureester", Helvetica Chiriica Acta, vol. 42, No. 4 (1959) 1356-1367 (with English abstract).

International Search Report and Written Opinion for PCT/EP2012/003571 mailed Nov. 29, 2012, 13 pages.

Van Leeuwen, F.F., et al., "Synthesis of the 2-ethyl-3-methylsuccinic acids via a stereospecific malonic ester alkylation" Laboratory of Organic Chemistry, Technisch Hogeschool Delft, Julianalaan 136, 2628 BL Delft, NL (received Jul. 18, 1979) 4 pages.

* cited by examiner

*Primary Examiner* — Sudhakar Katakam
(74) *Attorney, Agent, or Firm* — Cantor Colburn LLP

(57) ABSTRACT

The invention relates to a process for preparing (2,3) disubstituted succinates that allows (2,3) disubstituted succinates to be obtained in good purity and with acceptable reaction yields. The (2) and (3) substitutions may be the same or different. The process comprises reacting a haloacetate with a malonic acid ester into a tricarboxylate, which is further reacted to a (2,3) disubstituted tricarboxylate, hydrolyzed, decarboxylated and optionally esterified. Esterified (2,3) disubstituted succinic esters may be used as internal donor in Ziegler-Natta type catalysts for the polymerization of olefins.

11 Claims, No Drawings

PROCESS FOR PREPARING DI-SUBSTITUTED SUCCINATES

This application is a national stage application of PCT/EP2012/003571, filed Aug. 23, 2012, which claims priority from European application EP11007014.1, filed Aug. 29, 2011, both of which are hereby incorporated by reference in their entirety.

The present invention generally relates to a process for preparing 2,3 disubstituted succinates, such as succinic esters. More specifically, the present invention relates to a process for preparing 2,3 disubstituted succinates wherein the 2,3 substitutions are the same or different and may be alkyl or alkylaryl groups. More in particular does the present invention relate to a process for preparing a 2,3 dialkyl succinate, such as a 2,3 dialkyl succinic ester.

The invention further relates to the products obtained by said process. The present invention also relates to a process for olefin polymerisation in the presence of a Ziegler-Natta catalyst system comprising said di-substituted succinates as electron donor and optionally a cocatalyst.

Processes for preparation of dialkyl substituted succinates are already known in the art. For example, in *Synthetic communications*, 11(9), 687-697 (1981) it is disclosed the reaction of one or two equivalents of lithium dienolate of diethyl succinate with an alkylating agent at a reaction temperature of −78° C., followed by quenching with dilute acid in order to recover an ester with low yields. The product obtained have the same (symmetrical) substituents on 2,3 position and is a mixture of mono-, di-, tri- and tetra-succinate substituents, which are difficult to separate by distillation due to close boiling points. Document U.S. Pat. No. 6,818,583 discloses a solid catalyst component for the polymerisation of olefins comprising Mg, Ti, halogen and an electron donor selected from succinates, such as diethyl 2,3-diisopropylsuccinate, diisobutyl 2,3-diisopropylsuccinate, di-n-butyl 2,3-diisopropylsuccinate, diisobutyl 2,3-dicyclohexyl-2-methylsuccinate. Such donors can be prepared by the method disclosed in the prior art document mentioned above, *Synthetic communications*, 11(9), 687-697 (1981).

*Tetrahedron Letters*, 23, 2009-2012 (1977) discloses a process for preparing alkylidene substituted succinic acid esters in yields of not higher than 79%, by the dimerization of ketene silyl acetals promoted by titanium tetrachloride, at a reaction temperature of −78° C. The obtained succinates have only symmetrical substituents on 2,3 position.

In *Journal of Chemical Society* 93, 4605 (1971) it is disclosed a process for preparing dimerized substituted succinate esters by reacting high cost starting materials specifically, lithium ester enolates with copper (II) salts, at a reaction temperature of −78° C. Disubstituted succinates having only symmetrical substituents on 2,3 position and at yields of not higher than 81% are obtained.

*Journal of Organic Chemistry*, 61, 2809 (1996) discloses the synthesis of dl- and meso-2,3-diphenylsuccinic acid esters, having only symmetrical substituents on 2,3 position, by oxidative coupling of phenylacetic acid esters, at a reaction temperature of −45° C. The coupling reactions are typically influenced by steric congestion on the reacting carbon.

US2003/0181743A1 discloses a process for preparing alkylidene substituted succinic acid esters comprising step a) in which is carried out the reaction of a carbonilic compound e.g. acetone, a succinic acid and a base in a reaction medium and step b) in which the alkylidene substituted product obtained in step a) is esterified. The succinic ester and the base are used in certain amounts; the base is selected from metal hydrides and alkoxides; and the reaction medium comprises an aprotic or a protic liquid medium having a Ka, measured in water, lower than i-PrOH. The process according to US 2003/0181743 requires as raw material either an aldehyd or a ketone which are not easy available, are costly and/or require separate synthesis. In addition to that the process is based on so called Stobbe reactions which will result in alkylinede substituents. In order to obtain an alkyl substituent therefore a reduction step is required.

In *Recueil, Journal of the Royal Netherlands Chemical Society*, 9913, March 1980 it is disclosed a reaction of (−)-(S)-methyl 2-bromopropionate (4) (obtained from L-alanine) with dibenzyl ethylmalonate to give stereospecifically, in four steps, (+)-(2R,3S)-2-ethyl-3-methylsuccinic acid and its diastereoisomer. The malonic ester alkylation proceeded with so called Walden inversion. In *Helvetica Chimica Acta*, vol. 42, no. 4, 1959, pages 1356-1367 it is described the preparation of diethyl α-ethoxymethylene-succinate from diethyl-α-formyl-succinate.

The objective of the present invention is to provide a process by which symmetrical (2,3 positions substituted with the same groups) or asymmetrical (2,3 positions substituted with different groups) 2,3-substituted succinates such as succinic acid esters can be prepared at relatively low reaction temperatures and at acceptable reaction yields.

This object is achieved according to the invention with the process according to claim 1.

An advantage of the process according to the present invention is that it allows obtaining reaction products in good purity. A further advantage of the process according to the present invention is that it allows obtaining of the same or different substituents at the 2,3-positions of succinic acid esters. A further advantage of the process according to the present invention is that it avoids the need for coupling reactions that would be influenced by steric congestion on reacting carbon, which coupling reactions require costly raw materials. A further advantage of the process according to the present invention is that it allows the use of readily available, non-toxic and low cost raw materials or reagents.

The general scheme of the process according to the present invention can be illustrated as follows:

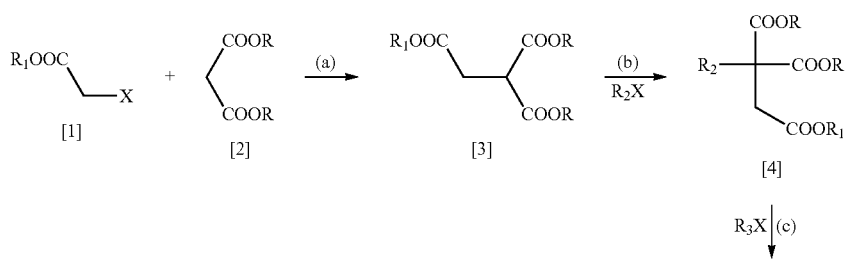

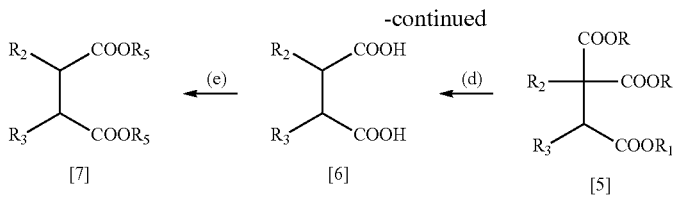

The general scheme for preparing 2,3 substituted succinates will now be further explained.

Step a) comprises the reacting of a compound [1] having the general formula

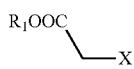

Such compounds are referred to as haloacetates. An example is ethylchloroacetate.

With a compound [2] having the general formula

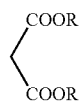

in the presence of a reaction medium and a base.

Such a compound [2] is referred to as malonic acid esters. An example is diethylmalonate.

R and R1 may be the same or different and are selected from the group consisting of branched or linear $C_1$-$C_{10}$ hydrocarbons, preferably linear, $C_1$-$C_{10}$ hydrocarbons. R and R1 are preferably selected from the group consisting of methyl, ethyl, n-propyl, n-butyl. The present inventors have found that $C_1$-$C_4$ hydrocarbons are preferred over $C_5$-$C_{10}$ hydrocarbons because of either their availability, solubility or reactivity.

X is a halogen element. Preferably, X is selected from Cl, Br and I. More preferably, X is Cl.

Compound [1] is used in amount of 0.9-1.1 equivalents of compound 2, preferably 1 equivalent. Equivalent as used herein means molar equivalent, i.e. that preferably 1 mol of compound [1] is used per mol of compound [2].

Compound [2] is used in amount of 0.9-1.1 equivalents of compound 1, preferably 1 equivalent.

If the used amount of compound [1] exceeds 1.1 then the risk for formation of dimer impurities in the reaction product, compound [3], increases.

The temperature for carrying out the step a) may range from 40-150° C. Preferably, the temperature applied in step a) ranges from 60-80° C. as high yields of the reaction product, compound [3], are obtained. Such temperatures are considered relatively low.

In step b) and respectively c), the reaction product of step a), i.e. compound [3], is further reacted in a step b) with a compound having general formula R2-X and in a step c) with a compound having general formula R3-X. Both reactions steps b) and c) are carried out in presence of a base and a reaction medium. The reaction product is compound [5].

R2 and R3 may be the same or different and are selected from the group consisting of $C_1$-$C_{20}$ linear or branched alkyl, alkenyl, cycloalkyl, and alkylaryl, optionally containing heteroatoms.

Preferably R2 and R3 are the same or different and selected from the group consisting of $C_1$-$C_8$ linear or branched alkyl, cycloalkyl and alkylaryl groups.

More preferably R2 and R3 are the same or different and are primary alkyls, in particular branched primary alkyls.

Examples of suitable R2 and R3 groups are methyl, ethyl, n-propyl, n-butyl, isobutyl, neopentyl, 2-ethylhexyl. Particularly preferred are ethyl, isobutyl, and neopentyl. In an embodiment R2 and R3 are the same or different and selected from the group consisting of $C_3$-$C_6$ cycloalkyl, benzyl and substituted benzyl, such as 4-methyl benzyl.

Although the compound [5] in the general reaction scheme is shown to have one R2 group and one R3 group, said compound [5] formed in steps (b) and (c) may also be a mixture of molecules, wherein the molecules in the mixture can contain two R2 groups (instead of one R2 and one R3 group), two R3 groups (instead of one R2 and one R3 group), or one R2 group and one R3 group. The amounts of R2-X and R3-X are preferably selected such that in compound [5] the average molar ratio between R2 and R3 is from about 1 to about 2, preferably from about 1.1 to about 1.5. Average molar ratio as used herein is to be understood as the total molar amount of R2 groups divided by the total molar amount of R3 groups in the molecules constituting the mixture of compound [5] that is formed. For instance, R2-X can be in a range of about 1 to 2 moles, preferably of about 1.3 to 1.7 moles with respect of compound [3]. R3-X can be in a range of about 1 to 2 moles, preferably of about 1.2 to 1.6 moles with respect of compound [4].

Preferably, R2 and R3 are independently selected from methyl, ethyl, isopropyl, cyclopentyl, isobutyl and benzyl groups.

The base used in steps a), b) and c) may be the same or different and is preferably selected from metal hydrides having formula MH and metal alkoxides of formula $MOR_4$ wherein M is a metal of Group I of the Periodic Table of elements, O is oxygen and R4 is selected from $C_1$-$C_{15}$ hydrocarbon groups. Preferably R4 is selected from $C_1$-$C_5$ alkyl groups. Preferably, M is sodium or potassium and more preferably, M is sodium. Preferred alkoxides include potassium ethoxide, sodium ethoxide, potassium tert-butoxide (t-BuOK) and sodium tert-butoxide (t-BuONa). More preferably, the base is sodium ethoxide. Preferably the base in steps b) and c) is the same. In an embodiment a metal alkoxide is used in step a) and a metal hydride is used in steps b) and c). Mixtures of metal hydride and metalalkoxides may also be applied.

The base may be added in amounts of 1-2.5 equivalents based on the amount of the respective starting materials compound [2], compound [3] and compound [4]. Preferably the amount of base is 1 equivalent in step a), 1.5 equivalent for step b) and 2.25-2.5 equivalent for step c).

The reaction medium may comprise aprotic or protic solvents. Preferably, the aprotic solvent is toluene, xylene, dimethylformamide (DMF), N,N-dimethylacetaamide, 1-methyl-2-pyrrolidine or tetrahydrofuran or a mixture of two or more of these. Most preferably, the aprotic solvent is toluene or DMF. Suitable examples of protic solvent include methyl alcohol, ethyl alcohol and 2-propanol. Preferably, the protic solvent is ethyl alcohol.

The temperature for carrying out step (b) and (c) ranges from 10-100° C., more preferably from 30-80° C.

In step d), compound [5] is first hydrolysed by an inorganic base such as NaOH and KOH and then decarboxylated by an inorganic acid, such as sulphuric acid or hydrochloric acid, preferably sulphuric acid of 40% concentration.

Esters are hydrolyzed by alkali metal hydroxides such as sodium hydroxide (NaOH) or potassium hydroxide (KOH) at boiling temperature of solvents like methanol or ethanol. Theoretically 1 equivalent of base is required for hydrolysis of one equivalent ester group. In the present invention there are three ester groups for hydrolysis. A suitable amount of base is three equivalents, preferably a 10% excess, i.e. 3.3 equivalents. Hydrolysis may take several hours for completion under reflux conditions.

Decarboxylation is carried out by heating the carboxylic acid with dilute inorganic acids such as sulphuric acid and hydrochloric acid. Concentration and strength of the acid determines the decarboxylation rate and completion. In general a strong acid at high concentration will result in fast and substantially complete decarboxylation.

Suitable solvents that may be used in step d) include protic solvents. Preferably, methyl alcohol, ethyl alcohol and 2-propanol are preferred. Ethyl alcohol is most preferred.

The amount of solvent is preferably about 5 to 15 milliliter (ml) per gram (gm) of compound [5].

The temperature for carrying out step (d) may range from 50-100° C., more preferably from 60° C. to 80° C.

The esterification reaction of step e) can be carried out by many methods employed in the prior art, such as esterification of a carboxylic acid using an alcohol catalysed by an acid. The preferred method for carrying out the esterification of compound [6] is by adding a compound of formula R5OH.

The choice for R5 depends on the type of ester that is desired and as such R5 may be is selected from a $C_1$-$C_{20}$ hydrocarbon, such as a linear or branched alkyl, alkenyl, cycloalkyl, alkylaryl group, optionally containing heteroatoms. Preferably R5 is a linear or branched $C_1$-$C_8$ alkyl, cycloalkyl or alkylaryl group.

Particularly preferred are the compounds in which R5 is selected from primary alkyls. Examples of suitable R5 groups are methyl, ethyl, n-propyl, n-butyl, isobutyl, neopentyl, 2-ethylhexyl. Particularly preferred are ethyl, isobutyl, and neopentyl group.

The temperature for carrying out step (e) may range from about 40 to about 110° C. The person skilled in art can select the optimum temperature within this range, according to boiling point of R5OH. For example for ethyl alcohol a temperature can be 78°-80° C. and for methanol the temperature can be 65°-66° C.

The invention further relates to the di-substituted succinates as directly obtained by said process.

The process for olefin polymerisation according to the present invention is carried out in the presence of a Ziegler-Natta catalyst system comprising said di-substituted succinates as internal electron donor and a cocatalyst.

Ziegler-Natta catalyst systems are well known in the art. The term normally refers to catalyst systems comprising a transition metal containing solid catalyst compound (a) and an organo-metal compound (b). Optionally one or more electron donor compounds (external donor) (c) may be added to the catalyst system as well.

The transition metal in the transition metal containing solid catalyst compound is normally chosen from groups 4-6 of the Periodic Table of the Elements (Newest IUPAC notation); more preferably, the transition metal is chosen from group 4; the greatest preference is given to titanium (Ti) as transition metal.

Although various transition metals are applicable, the following is focused on the most preferred one being titanium. It is, however, equally applicable to the situation where other transition metals than Ti are used. Titanium containing compounds useful in the present invention as transition metal compound generally are supported on hydrocarbon-insoluble, magnesium and/or an inorganic oxide, for instance silicon oxide or aluminum oxide, containing supports, generally in combination with an internal electron donor compound. The transition metal containing solid catalyst compounds may be formed for instance by reacting a titanium (IV) halide, an organic internal electron donor compound and a magnesium and/or silicon containing support. The transition metal containing solid catalyst compounds may be further treated or modified with an additional electron donor or Lewis acid species and/or may be subjected to one or more washing procedures, as is well known in the art.

Suitable magnesium-containing supports include magnesium halides; a reaction product of a magnesium halide such as magnesium chloride or magnesium bromide with an organic compound, such as an alcohol or an organic acid ester, or with an organometallic compound of metals of groups 1-3; magnesium alcoholates; or magnesium alkyls. One possible magnesium-containing support, described in U.S. Pat. No. 4,612,299 is based on at least one magnesium carboxylate prepared in a reaction between a hydrocarbyl magnesium (halide) compound with carbon dioxide. A second possible magnesium-containing support is described in U.S. Pat. No. 6,268,306. The compound described is obtained by reaction of metallic magnesium with an aromatic halide of which one reaction product is separated from the solid residual products and reacted with a silane compound containing an alkoxy or arylalkoxy group to a precipate a second reaction product. Optionally this second reaction product is then contacted with for instance a halogenated titanium compound to form a transition metal containing solid catalyst compound. Again another possible magnesium containing support is described in WO-A-98/45338. One solid catalyst component is synthesized through the reaction of anhydrous magnesium chloride with the mono ether epoxy-chloropropane and tributyl phosphate. The reaction mixture is reacted with phthalic anhydride at elevated temperature. Subsequently this magnesium containing support can optionally be reacted with titanium tetrachloride at low temperatures to yield a polymerization catalyst. Another example is given in U.S. Pat. No. 5,567,665. Herein the synthesis of a magnesium-containing support is cited by reacting a mixture of magnesium ethoxide with ethanol with carbon dioxide. The reaction product, a carboxylated magnesium ethoxide is then spray dried on silica and decarboxylated in the next reaction step by evaporation of carbon dioxide. In U.S. Pat. No. 5,066,737 another possible magnesium-containing support is cited. The magnesium-containing support is prepared by reacting magnesium ethoxide with titanium ethoxide and o-cresol in chlorobenzene. Subsequently the resulting reaction mixture is mixed with a magnesium-ethanol adduct and chlorobenzene to form the solid magnesium-containing support. In EP 1336625 A1 a catalyst component comprising a titanium containing compound, a magnesium compound and an inorganic support is cited. The catalyst component is prepared by reacting a silica gel with an organomagnesium compound and subsequent treatment with hydrogen chloride. In a next stage the obtained solid is treated with a titanium compound and optionally an internal donor to yield a transition metal containing solid catalyst compound. The transition metal containing solid catalyst compounds described above only are illustrative of many possible transition metal containing solid catalyst compounds that can be used in the process of the present invention. The invention is not limited to such examples.

Titanium (IV) containing compounds useful in preparing the transition metal containing solid catalyst compound preferably are titanium halides and haloalcoholates having 1 to about 20 carbon atoms per alcoholate group. Mixtures of titanium containing compounds can be employed if desired. Preferred titanium containing compounds are the halides and haloalcoholates having 1 to about 8 carbon atoms per alcoholate group. Examples of such compounds include $TiCl_4$, $TiBr_4$, $Ti(OCH_3)Cl_3$, $Ti(OC_2H_5)Cl_3$, $Ti(OC_4H_9)Cl_3$, $Ti(OC_6H_5)Cl_3$, $Ti(OC_6H_{13})Br_3$, $Ti(OC_8H_{17})Cl_3$, $Ti(OCH_3)_2Br_2$, $Ti(OC_2H_5)_2Cl_2$, $Ti(OC_6H_{13})_2Cl_2$, $Ti(OC_8H_{17})_2Br_2$, $Ti(OCH_3)_3Br$, $Ti(OC_2H_5)_3Cl$, $Ti(OC_4H_9)_3Cl$, $Ti(OC_6H_{13})_3Br$ and $Ti(OC_8H_{17})_3Cl$. Titanium tetrahalides, particularly titanium tetrachloride ($TiCl_4$), are most preferred.

The internal electron donors useful in the preparation of a stereo specific transition metal containing solid catalyst compound is obtained according to the process of the invention.

The internal electron donor may for instance be used in an amount ranging from about 0.001 to about 1.0 mol per gram atom of the transition metal and preferably from about 0.005 to about 0.8 mol. Best results are achieved when this ratio ranges from about 0.01 to about 0.6 mol per gram atom of the transition metal.

Although not required, the transition metal containing solid catalyst compound may be contacted with at least one Lewis acid prior to polymerization. Such Lewis acids are generally liquids at treatment temperatures and have a Lewis acidity high enough to remove impurities such as un-reacted starting materials and poorly affixed compounds from the surface of the above-described solid reaction product. Preferred Lewis acids include halides of group 4, 5, 13-15 metals which are in the liquid state at temperatures up to about 170° C. Specific examples of such materials include $BCl_3$, $AlBr_3$, $TiCl_4$, $TiBr_4$, $SiCl_4$, $GeCl_4$, $SnCl_4$, $PCl_3$ and $SbCl_5$. Preferred Lewis acids are $TiCl_4$ and $SiCl_4$. Mixtures of Lewis acids can be employed if desired. Such Lewis acid may be used in a compatible diluent.

In the case the transition metal containing solid catalyst compound comprises a transition metal supported on a magnesium containing support, it preferably contains from about 1 to about 6 wt. % transition metal, from about 10 to about 25 wt. % magnesium, and from about 45 to about 65 wt. % halogen, more preferably from about 1.0 to about 5 wt. % transition metal, from about 15 to about 21 wt. % magnesium, and from about 55 to about 65 wt. % chlorine.

In the case the transition metal containing solid catalyst compound comprises a transition metal, a magnesium compound and an inorganic oxide as support, it preferably contains from 1 to about 6 wt. % transition metal, from about 2 to about 20 wt. % magnesium and 20 to about 60 wt. % chlorine.

In the catalyst system for instance an organo-metal hydride and/or a metal alkyl compound is used as a co-catalyst. The metal in this compound is chosen from groups 1-3 and 12-13 of the Periodic Table of Elements. Preferred is a metal alkyl and, more preferred, an alkyl aluminum compound.

Preferred metal alkyls are, for instance, compounds of the formula $MR_m$ wherein M is chosen from groups 2, 12 or 13, each R is independently an alkyl radical of 1 to about 20 carbon atoms, and m corresponds to the valence of M. Examples of useful metals, M, include magnesium, calcium, zinc, cadmium, aluminum, and gallium. Examples of suitable alkyl radicals, R, include methyl, ethyl, butyl, isobutyl, hexyl, octyl, decyl, tetradecyl, and eicosyl.

From the standpoint of polymerization performance, preferred metal alkyls are those of magnesium, zinc, and aluminum wherein the alkyl radicals each may contain, for instance, 1 to about 12 carbon atoms. Specific examples of such compounds include $Mg(CH_3)_2$, $Mg(C_2H_5)_2$, $Mg(C_2H_5)(C_4H_9)$, $Mg(C_4H_9)_2$, $Mg(C_6H_{13})_2$, $Mg(C_{12}H_{25})_2$, $Mg(C_4H_9)(C_8H_{17})$, $Zn(CH_3)_2$, $Zn(C_2H_5)_2$, $Zn(C_4H_9)_2$, $Zn(C_4H_9)(C_8H_{17})$, $Zn(C_6H_{13})_2$, $Zn(C_{12}H_{25})_2$, $Al(CH_3)_3$, $Al(C_2H_5)_3$, $Al(C_3H_7)_3$, $Al(C_4H_9)_3$, $Al(C_6H_{13})_3$, and $Al(C_{12}H_{25})_3$. More preferably a magnesium, zinc, or aluminum alkyl containing 1 to about 6 carbon atoms per alkyl radical is used. Alkyl aluminum compounds are most preferred. Best results are achieved through the use of trialkylaluminums containing 1 to about 6 carbon atoms per alkyl radical, and particularly triethylaluminum and triisobutylaluminum or a combination thereof.

If desired, metal alkyls having one or more halogen or hydride groups can be employed, such as ethylaluminum dichloride, diethylaluminum chloride, ethylaluminum sesquichloride or diisobutylaluminum hydride.

In a catalyst system used in the polymerization process, typically, the organo-metal compound to transition metal atomic ratios are, for instance, about 10 to about 500 and preferably about 30 to about 300.

The transition metal containing solid catalyst compound used in this invention may be pre-polymerized with an α-olefin before use as a polymerization catalyst. In one embodiment of the pre-polymerization the transition metal compound and an organo-metal compound as a co-catalyst (for instance triethylaluminum) are contacted with an α-olefin (for instance propylene), preferably in the presence of an external electron donor (for instance a silane and preferably an organosilane). The pre-polymerization can be carried out in an inert hydrocarbon (for instance hexane), in liquid or in the gas phase. Typically, the polymer/catalyst weight ratio of the resulting pre-polymerized component is about 0.1:1 to about 20:1. Pre-polymerization forms a coat of polymer around the catalyst particles, which in many instances improves the particle morphology, activity, stereo specificity, and attrition resistance. A particularly useful pre-polymerization procedure is described in U.S. Pat. No. 4,579,836.

Optionally, an external electron donor is present in the catalyst system, meaning that this compound is added to the reaction system, and not used in the preparation of the transition metal containing solid catalyst compound (vide a) supra). External electron donor compounds used in the process of the present invention can be organic compounds containing one or more atoms of oxygen, nitrogen, sulphur and phosphorus. Such compounds include mono- and polyfunctional organic acids, organic acid esters, alcohols, ethers, aldehydes, ketones, amines, amine oxides, amides, thiols and various phosphorus acid esters and amides, and the like. Mixtures of external electron donors can be used if desired. Preferred external electron donor compounds are organosilane compounds of general formula: $R^1_q Si(OR^2)_{4-q}$ (in which each $R^1$ independently may represent a $C_{1-20}$-alkyl, cycloalkyl, phenyl, vinyl, allyl, or aryl group optionally containing heteroatoms; each $R^2$ independently may represent a $C_{1-4}$-alkyl, cycloalkyl, phenyl, vinyl, allyl, or aryl group optionally containing one or more, preferably 1-3, heteroatoms, for instance O, S and P; and q represents 0 or an integer of from 1 to 3). Examples of such organosilane compounds are alkylalkoxysilanes, arylalkoxysilanes, aryl(cyclo)alkylalkoxysilanes, (cyclo)alkylalkoxysilanes, or mixtures thereof, for instance diisopropyldimethoxysilane, diisobutyldimethoxysilane, isobutylisopropyldimethoxysilane, dicyclohexyldimethoxysilane, diphenyldimethoxysilane, phenylmethyldiethoxysilane, cyclohexylmethyldimethoxysilane, ethyltriethoxysilane, dicyclopentyldimethoxysilane, propyltrimethoxysilane, phenyltrimethoxysilane.

The external donor, if added at all, is usually added to the other catalyst system components or added separately to the polymerization reactor, preferably in a molar ratio relative to the transition metal of from 0.1:1 to 250:1.

Crystalline poly-α-olefins can be prepared by contacting at least one α-olefin with a Ziegler Natta catalyst system under polymerization conditions. Such conditions include polymerization temperature and time, monomer pressure, avoidance of contamination of catalyst, choice of polymerization medium in slurry processes, the use of ingredients (like hydrogen) to control polymer molecular weights, and other conditions well known to persons of skill in the art. Slurry-, bulk-, and gas-phase polymerization processes or combinations of the latter in a multistage process are contemplated herein.

The amount of catalyst to be employed varies depending on the choice of polymerization technique, reactor size, monomer to be polymerized, and other factors known to persons skilled in the art. Typically, catalysts are used in amounts ranging from about 0.2 to 0.02 milligrams of catalyst to gram of polymer produced.

Irrespective of the polymerization process employed, polymerization preferably will be carried out at temperatures sufficiently high to ensure reasonable polymerization rates and avoid unduly long reactor residence times, but not so high as to result in the production of unreasonably high levels of stereo random products with problems of stickiness and bad morphology. Generally, temperatures range from about 40° C. to about 150° C. with about 60° C. to about 100° C. being preferred from the standpoint of attaining good catalyst performance and high production rates.

The polymerization preferably is carried out at monomer pressures of about atmospheric or above. Generally, monomer pressures range from about 0.1 to 5 MPa although in gas phase polymerizations, monomer pressures should not be below the vapor pressure at the polymerization temperature of the α-olefin(s) to be polymerized. The polymerization time will generally range from about ½ to several hours in batch processes with corresponding average residence times in continuous processes. Polymerization times ranging from about 1 to about 4 hours are typical in autoclave-type reactions. In slurry processes, the polymerization time can be regulated as desired. Polymerization times ranging from about ½ to several hours are generally sufficient in continuous slurry processes and gas phase processes. Diluents suitable for use in slurry polymerization processes include alkanes and cycloalkanes (such as pentane, hexane, heptane, n-octane, isooctane, cyclohexane, and methylcyclohexane); alkyl aromatics (such as toluene, xylene, ethyl benzene; isopropyl benzene, ethyl toluene, n-propyl-benzene, diethyl benzenes, and mono- and dialkylnaphthalenes); halogenated and hydrogenated aromatics (such as chlorobenzene, chloronaphthalene, orthodichlorobenzene, tetrahydronaphthalene, decahydronaphthalene); high molecular weight liquid paraffins or mixtures thereof, and other well-known diluents. It often is desirable to purify the polymerization medium prior to use, for instance by distillation, percolation through molecular sieves, contacting with a compound such as an alkyl aluminum compound capable of removing trace impurities, or by other suitable means.

Examples of gas-phase polymerization processes include both stirred bed reactors and fluidized bed reactor systems; such processes are well known in the art. Typical gas phase α-olefin polymerization reactor systems comprise a reactor vessel to which α-olefin monomer(s) and a catalyst system can be added and which contain an agitated bed of forming polymer particles. Typically, the components of the catalyst system are added together or separately through one or more valve-controlled ports in the reactor vessel. α-Olefin monomer, typically, is provided to the reactor through a recycle gas system in which un-reacted monomer removed as off-gas and fresh feed monomer are mixed and injected into the reactor vessel. A quench liquid which can be liquid monomer, can be added to the polymerizing α-olefin through the recycle gas system in order to control temperature.

It is well known that α-olefin polymers can be exothermically produced as powders in fluidized bed reactors wherein the fluidization is provided by a circulating mixture of gases that includes the monomer(s). The fluidizing gases leaving the reactor can be re-circulated with cooling before reintroduction to the reactor in order to remove the heat of reaction and keep the fluidized bed temperature at the desired temperature. Preferably (a portion of) the re-circulating stream (the off gas) is cooled to condense a portion of said gas to liquid, after which the condensed and cooled products are (at least partially) recycled to the reactor. It is advantageous to remove the latent heat of vaporization, in addition to the sensible heat accumulated in the gas, since the latent heat of vaporization is much larger per degree of cooling than the sensible heat of the uncondensed stream.

Irrespective of polymerization technique, polymerization is carried out under conditions that exclude oxygen, water, and other materials that act as catalyst poisons.

Although not usually required, upon completion of polymerization, or when it is desired to terminate polymerization or deactivate the catalyst system in the process of the present invention, the polymer can be contacted with water, alcohols, oxygen, acetone, or other suitable catalyst deactivators in a manner known to persons skilled in the art.

In the context of present invention, an olefinic monomer is understood to be a molecule containing at least one polymerisable double bond. Suitable olefinic monomers are $C_2$-$C_{20}$ olefins. Preferred monomers include ethylene and $C_{3-12}$ alpha-olefins which are substituted or unsubstituted by up to two $C_{1-6}$ alkyl radicals, $C_{8-12}$ vinyl aromatic monomers which are substituted or unsubstituted by up to two substituents selected from the group consisting of $C_{1-4}$ alkyl radicals and $C_{4-12}$ straight chained or cyclic hydrocarbyl radicals which are substituted or unsubstituted by a $C_{1-4}$ alkyl radical. Illustrative non-limiting examples of such alpha-olefins are propylene, 1-butene, 1-pentene, 1-hexene, 1-heptene, 1-octene, 1-nonene, 1-decene, 1-undecene, 1-dodcene, 1-tridecene, 1-tetradecene, 1-pentadecene, 1-hexadecene, 1-heptadecene, 1-nonadecene, 1-eicosene, 3-methyl-1-butene, 3-methyl-1-pentene, 3-ethyle-1-pentene, 4-methyl-1-pentene, 4-methyl-1-hexene, 4,4-dimethyl-1-hexene, 4,4-dimethyl-1-pentene, 4,4-ethyl-1-hexene, 3-ethyl-1-hexene, 9-methyl-1-decene. These olefins may be also used in combination. More preferably, ethylene and propylene are used according to the present invention. Most preferably, the polyolefin is ethylene homopolymer or copolymer. The amount of olefin used for the polymerization process may not be less than 20 mol % of the whole components in the polymerization vessel, preferably not less than 50 mol %. The comonomer is preferably a $C_3$ to $C_{20}$ linear, branched or cyclic monomer, and in one embodiment is a $C_3$ to $C_{12}$ linear or branched alpha-olefin, preferably propylene, hexene, pentene, hexene, heptene, octene, nonene, decene, dodecene, 4-methyl-pentene-1,3-methyl pentene-1,3,5,5-trimethyl hexene-1, and the like. The amount of comonomer used for the copolymerization process may not be more than 50 wt. % of the used monomer, preferably not more than 30 wt. %.

The obtained polymer or resin may be formed into various articles, including bottles, drums, toys, household containers, utensils, film products, fuel tanks, pipes, geomembranes and liners. Various processes may be used to form these articles, including blow moulding, extrusion moulding, rotational moulding, thermoforming, cast moulding and the like. After polymerisation, conventional additives and modifiers can be added to the polymer to provide better processing during manufacturing and for desired properties of the desired product. Additives include surface modifiers, such as slip agents, antiblocks, tackifiers; antioxidants, such as primary and secondary antioxidants, pigments, processing aids such as waxes/oils and fluoroelastomers; and special additives such as fire retardants, antistatics, scavengers, absorbers, odor enhancers, and degradation agents. The additives may be present in the typically effective amounts well known in the art, such as $1 \times 10^{-6}$ wt. % to 5 wt. %.

The invention will be further explained by the following non-limiting examples.

Example I

Preparation of Triethyl ethane-1,1,2-tricarboxylate (Compound [3])

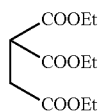

Step a):

Sodium metal (23 gram, 1 mole) was dissolved in dry ethanol (500 ml) with stirring. To this 160 gram (1 mole) of diethyl malonate (compound [2]) was added in 30 minutes. The reaction mixture was cooled to 15° C. and ethyl chloroacetate (compound [1], 117 gm, 0.095 mole) was then added drop wise in 30 minutes. On completion of addition the reaction mass was refluxed for 6 hours and then poured in 2 liters of water. The organic materials were extracted with dichloromethane (three times with 500 ml). Next, the organic extracts were dried over sodium sulfate, filtered and evaporated to give an oily substance which was then vacuum distilled to give 220 gm (89% of the theoretical maximum yield) of triethyl ethane-1,1,2-tricarboxylate, compound [3].

Example II

Diethyl 2,3-bis(2-methylpropyl)butanedioate (Compound [7])

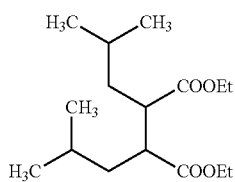

Step-b): Preparation of triethyl 4-methylpentane-1,2,2-tricarboxylate, compound [4].

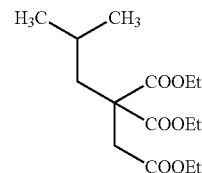 [SMILES: CCOC(=O)CC(CC(C)C)(C(=O)OCC)C(=O)OCC]

Sodium hydride (21 gram, 0.482 mole) was added to 200 ml dimethylformamide at 20° C. under nitrogen atmosphere. Then 80 grams (0.325 mole) of triethyl ethane-1,1,2-tricarboxylate (compound [3] made in example I) was added to the solution at a temperature of below 30° C. The reaction mixture was maintained at room temperature for 4 hours and 52 ml (0.482 mole) of isobutyl bromide (R2-X) was added drop wise after which the reaction mixture was stirred for another 20 hours at room temperature. When the reaction was complete 1 liter of cold water was added and the organic materials were extracted with dichloromethane (500 ml). The organic extracts were dried over sodium sulfate filtered and evaporated to give an oily substance, which was vacuum distilled to give 88 gram (89% of the theoretical maximum yield) triethyl 4-methylpentane-1,2,2-tricarboxylate, compound [4].

The above purified material, compound [4], was used for step c):

Sodium hydride (4.5 gram, 0.103 mol) was added to dimethylformamide (50 ml) at 20° C. under nitrogen atmosphere. The reaction mixture was heated to 55° C. and 20 gram (0.066 mol) of triethyl 4-methylpentane-1,2,2-tricarboxylate was added drop wise. The reaction mixture was then maintained at 55° C. for 3 hours.

The temperature was increased to 85° C. and 9.3 ml (0.088 mole) of isobutyl bromide, $R_3$—X, was added. The reaction mixture was maintained at 85° C. for another 10 hours. When the reaction was complete 200 ml of cold water was added and the organic materials were extracted with dichloromethane (250 ml). The organic extract was dried over sodium sulfate filtered and evaporated to give 22 gram (93% of the theoretical maximum yield) of a crude, compound [5].

Step d):

The crude prepared in step c) above was added to 14 gram (0.248 mole) of KOH in a 175 ml ethanol solution and was heated to reflux for 15 hours. After completion of the hydrolysis reaction the solvent was evaporated. Next, sulfuric acid solution was added (30 gram, 0.3 mole of sulfuric acid in 80 ml water) and the reaction mixture was heated to reflux for decarboxylation for 15 hours.

The reaction mixture was cooled to room temperature and extracted in dichloromethane (200 ml). The organic extract was dried over sodium sulfate, filtered and evaporated to give 11 gm (86% of the theoretical maximum yield) diacid with general formula of compound [6].

Step e):

The obtained diacid of step d) was esterified with 70 ml ethanol and 1 ml sulfuric acid at reflux temperature for 12 hours. On completion of reaction ethanol was evaporated and dichloromethane (100 ml) was added. The mixture was washed with saturated sodium bicarbonate to neutralize the mixture to a pH of about 7. The dichloromethane layer was separated and dried over sodium sulfate, filtered and evaporated to give 11 gram of an oily substance (85% of the theoretical maximum yield) of diethyl 2,3-bis(2-methylpropyl) butanedioate, compound [7].

($^1$HNMR 300 MHz, CDCl3) δ 4.19-4.08 (4H, m); 2.71-2.62 (2H, m); 1.79-1.40 (4H, m); 1.28-1.22 (6H, t); 1.10-1.05 (1H, m); 0.9-0.85 (12H, m)

$^{13}$CNMR: δ174.64, 174.49, 60.60, 47.27, 46.19, 40.16, 38.65, 26.66, 26.56, 23.99, 23.95, 21.81, 21.65, 14.64, 14.59

Example III

Diethyl 2-ethyl-3-(2-methylpropyl)butanedioate (Compound [7])

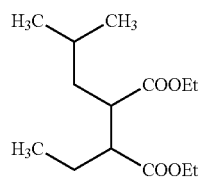

Step c):

Sodium hydride (4.8 gram, 0.11 mol) was added under nitrogen at room temperature to 50 ml of dimethylformamide. The reaction mixture was heated to 55° C. and 20 gram (0.066 mole) of triethyl 4-methylpentane-1,2,2-tricarboxylate, Compound [4], was added drop wise, after which the mixture was maintained at 50-55° C. for 3 hours.

Next, 8 ml of ethyl bromide (0.107 mole) was added and the reaction mixture was maintained at 50-55° C. for 7 hours. When the reaction was complete 200 ml of cold water was added and organic materials were extracted with dichloromethane (250 ml). The organic extract was dried over sodium sulfate filtered and evaporated to give 19 gram of an oily substance (87% of the theoretical maximum yield) (compound [5]) is obtained.

Step d):

The compound [5] prepared above was added to a solution of 16 gram (0.28 mole) KOH in 175 ml ethanol and was heated to reflux for 15 hours. After completion of the hydrolysis reaction the solvent was evaporated. Next, sulfuric acid solution was added (30 gram, 0.3 mole of sulfuric acid in 80 ml water) and the reaction mixture was heated to reflux for decarboxylation for 15 hours.

The reaction mixture was cooled to room temperature and extracted in dichloromethane (200 ml). The organic extract was dried over sodium sulfate, filtered and evaporated to give 12 gm (92% of the theoretical maximum yield) diacid with general formula of compound [6].

Step e):

The obtained diacid of step d) was esterified with 70 ml ethanol and 1 ml sulfuric acid at reflux temperature for 12 hours. On completion of reaction ethanol was evaporated and dichloromethane (100 ml) was added. The mixture was washed with saturated sodium bicarbonate to neutralize the mixture to a pH of about 7. The dichloromethane layer was separated and dried over sodium sulfate, filtered and evaporated to give 13 gram of an oily substance (90% of the theoretical maximum yield) of diethyl 2-(2-methylpropyl)-3-ethyl-butanedioate, compound [7].

($^1$HNMR 300 MHz, CDCl3) δ 4.17-4.10 (4H, m); 2.4-2.8 (2H, m); 1.4-1.8 (5H, m); 1.4-1.6 (6H, m); 0.877 (9H, m)

$^{13}$CNMR: δ175.019, 60.63, 50.75, 49.29, 46.62, 44.93, 40.38, 38.97, 26.71, 24.25, 24.074, 22.47, 21.80, 21.66, 14.69, 14.59, 12.095, 11.72

Example IV

Diethyl 2-benzyl-3-(2-methylpropyl)butanedioate (Compound [7])

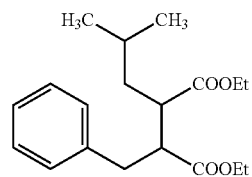 [SMILES: CCOC(=O)C(Cc1ccccc1)C(CC(C)C)C(=O)OCC]

Sodium hydride (4.5 gram, 0.103 mol) was added under nitrogen atmosphere to 50 ml of dimethylformamide. The reaction mixture is heated to about 55° C. and 20 gram (0.066 mole) of Triethyl 4-methylpentane-1,2,2-tricarboxylate, compound [4], was added drop wise. The reaction mixture was maintained at this temperature 3 hours.

Then, 15 gram of Benzyl bromide (0.0877 mole) was added and the reaction mixture was maintained at a temperature of 55° C. for 7 hours. Cold water (500 ml) was then added to the reaction mixture and organic material was extracted with dichloromethane (250 ml). The organic extract was dried over sodium sulfate and filtered after which solvent was evaporated. The procedure yielded 22 gram of oily substance 22 gm (85% of the theoretical maximum yield), compound [5].

Step d):

The compound [5] prepared above was added to a solution of 14 gram (0.248 mole) KOH in 175 ml ethanol and was heated to reflux for 15 hours. After completion of the hydrolysis reaction the solvent was evaporated. Next, sulfuric acid solution was added (30 gram, 0.3 mole of sulfuric acid in 80 ml water) and the reaction mixture was heated to reflux for decarboxylation for 15 hours.

The reaction mixture was cooled to room temperature and extracted in dichloromethane (200 ml). The organic extract was dried over sodium sulfate, filtered and evaporated to give 13 gm (88% of the theoretical maximum yield) diacid with general formula of compound [6].

Step e):

The obtained diacid of step d) was esterified with 70 ml ethanol and 1 ml sulfuric acid at reflux temperature for 12 hours. On completion of reaction ethanol was evaporated and dichloromethane (100 ml) was added. The mixture was washed with saturated sodium bicarbonate to neutralize the mixture to a pH of about 7. The dichloromethane layer was separated and dried over sodium sulfate, filtered and evaporated to give 14 gram of an oily substance (91% of the theoretical maximum yield) of diethyl 2-(2-methylpropyl)-3-ethyl-butanedioate, compound [7].

($^1$HNMR 300 MHz, CDCl3) δ7.19-7.029 (5H, m); 4.12-3.85 (4H, m); 2.88-2.68 (4H, m); 1.69-1.20 (3H, m); 1.17 (6H, m); 0.81-0.78 (6H, m)

$^{13}$CNMR: δ174.43, 173.49, 139.125, 138.717, 129.23, 129.055, 128.506, 126.65, 126.59, 60.78, 60.65, 51.15, 49.88, 46.80, 45.24, 40.07, 38.78, 37.20, 35.57, 26.69, 23.95, 14.69

The invention claimed is:
1. A process for preparing a 2,3 disubstituted succinate comprising the steps of:
a) reacting a compound [1] of formula

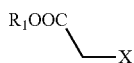

with a compound [2] of formula

to form a compound [3] of formula

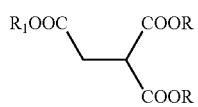

followed by
b) reacting compound [3] with a compound of formula R2-X to form a compound [4] of formula

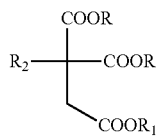

and
c) reacting compound [4] with a compound of formula R3-X to form a 2,3 disubstituted tricarboxylate compound [5] of formula

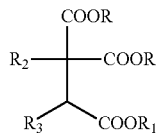

followed by
d) first hydrolysing compound [5] using an inorganic base and then decarboxylating the hydrolysed compound using an inorganic acid to yield a 2,3 disubstituted succinic acid compound [6] of formula

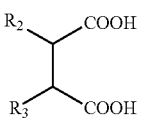

wherein R and R1 may be the same or different and are selected from the group consisting of branched or linear $C_1$-$C_{10}$ hydrocarbons, and
R2 and R3 may be the same or different and are selected from the group consisting of $C_1$-$C_{20}$ linear or branched alkyl, alkenyl, cycloalkyl, and alkylaryl, optionally containing heteroatoms, and
X is a halogen,
wherein the steps a), b) and c) are carried out in the presence of a base which may be the same or different for each of said steps.

2. The process according to claim 1 further comprising a step e) wherein at least one carboxylic acid group of compound [6] is esterified using a compound of general formula R5-OH to obtain compound [7],

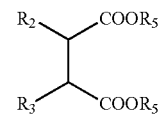

wherein R5 is a $C_1$-$C_{20}$ linear or branched alkyl, alkenyl, cycloalkyl or alkylaryl group, optionally containing heteroatoms.

3. The process according to claim 1 wherein compound [1] is used in an amount of 0.9-1.1 equivalents of compound [2].

4. The process according to claim 1 wherein the amounts of R2-X and R3-X in steps b) and c) respectively are chosen such that in compound [5] an average molar ratio between R2 and R3 is from about 1 to about 2.

5. The process according to claim 1 wherein steps b) and c) are carried out in a reaction medium comprising a protic solvent.

6. The process according to claim 1 wherein the base is a metal hydride having formula MH or a metal alkoxide of formula MOR4, wherein M is a metal of Group I of the Periodic Table of elements and R4 is selected from $C_1$-$C_{15}$ hydrocarbon groups.

7. The process according to claim 6 wherein M is sodium or potassium.

8. The process according claim 1 wherein the base is a metal alkoxide in step a) and a metal hydride in steps b) and c).

9. The process according to claim 1 wherein the base in steps a), b) and c) is added in an amount of 1-2.5 equivalents based on the amount of the respective starting materials compound [2], compound [3] and compound [4].

10. The process according claim 1 wherein the temperature in step a) is from 40° C. to 150° C. and wherein the temperature in steps b) and C) is from 10° C. to 100° C. and wherein the temperature in step d) is from 50° C. to 100° C. and wherein the temperature in step e) is from 40° C. to 110° C.

11. Method for preparing a Ziegler Natta type catalyst comprising preparing the 2,3 disubstituted succinate according to claim 2 and reacting said 2,3 disubstituted succinate with a transition metal compound and a magnesium or silica containing support.

* * * * *